US012336891B2

(12) United States Patent
Liu et al.

(10) Patent No.: US 12,336,891 B2
(45) Date of Patent: Jun. 24, 2025

(54) APERTURED NONWOVEN WEB AND METHOD OF FORMING THE SAME

(71) Applicant: The Procter & Gamble Company, Cincinnati, OH (US)

(72) Inventors: Zhe Liu, Beijing (CN); Lifeng Zhao, Beijing (CN); Ruizhi Pei, Beijing (CN); Junqin Zheng, Guangzhou (CN)

(73) Assignee: The Procter & Gamble Company, Cincinnati, OH (US)

( * ) Notice: Subject to any disclaimer, the term of this patent is extended or adjusted under 35 U.S.C. 154(b) by 1097 days.

(21) Appl. No.: 17/159,243

(22) Filed: Jan. 27, 2021

(65) Prior Publication Data
US 2021/0236344 A1 Aug. 5, 2021

Related U.S. Application Data

(63) Continuation of application No. PCT/CN2020/074093, filed on Jan. 31, 2020.

(51) Int. Cl.
*A61F 13/15* (2006.01)
*A61F 13/512* (2006.01)
(Continued)

(52) U.S. Cl.
CPC .. *A61F 13/15707* (2013.01); *A61F 13/15764* (2013.01); *A61F 13/512* (2013.01);
(Continued)

(58) Field of Classification Search
CPC .......... A61F 13/15707; A61F 13/15764; A61F 13/512; A61F 13/5146; A61F 2013/15715;
(Continued)

(56) References Cited

U.S. PATENT DOCUMENTS 3,679,535 A * 7/1972 Kalwaites .............. D04H 1/495
28/105
4,726,976 A * 2/1988 Karami ................... B32B 27/12
428/137
(Continued)

FOREIGN PATENT DOCUMENTS

CN 1964685 A 5/2007
CN 101152114 A 4/2008
(Continued)

OTHER PUBLICATIONS

Hashino, Absorbent Article, 120/01/2016, Espacenet Translation (Year: 2016).*
(Continued)

*Primary Examiner* — Nicholas J. Weiss
*Assistant Examiner* — Brandon W. Levy
(74) *Attorney, Agent, or Firm* — Christian M. Best

(57) ABSTRACT

A nonwoven web with apertures, suitable for use in a disposable absorbent article, is disclosed. Also disclosed is a method of producing a nonwoven web with apertures. The nonwoven web comprises greater than 50%, by weight of the web, of thermoplastic fibers. Each of the aperture is defined by an opening in a first surface of the nonwoven web and a side wall. The side walls of the apertures have a mean height of less than 460 μm. Also disclosed is an absorbent article comprising the nonwoven web. A topsheet, backsheet, or other component of the absorbent article may comprise the nonwoven web.

13 Claims, 9 Drawing Sheets

(51) Int. Cl.
*A61F 13/514* (2006.01)
*A61F 13/51* (2006.01)
(52) U.S. Cl.
CPC .... *A61F 13/5146* (2013.01); *A61F 2013/15715* (2013.01); *A61F 2013/15934* (2013.01); *A61F 2013/51026* (2013.01); *A61F 2013/51452* (2013.01)
(58) Field of Classification Search
CPC .. A61F 2013/15934; A61F 2013/51026; A61F 2013/51452; A61F 13/15577; A61F 13/51121; A61F 13/15731; A61F 13/511; A61F 13/51104; D04H 1/43828; D04H 1/5412; D04H 1/55; D04H 1/74; D04H 1/4391; D04H 1/544; Y10T 428/24273; Y10T 428/24322; Y10T 428/2904; B32B 2307/728; B32B 2555/02; B32B 5/022; B32B 3/266
See application file for complete search history.

(56) References Cited

U.S. PATENT DOCUMENTS

| | | | | |
|---|---|---|---|---|
| 5,643,240 | A * | 7/1997 | Jackson | ............ A61F 13/51121 |
| | | | | 604/383 |
| 2010/0310810 | A1* | 12/2010 | Bond | ........................ B32B 5/22 |
| | | | | 428/74 |

FOREIGN PATENT DOCUMENTS

| | | | | |
|---|---|---|---|---|
| CN | 102844006 | A | 12/2012 | |
| CN | 103492170 | A | 1/2014 | |
| CN | 106687090 | A | 5/2017 | |
| CN | 107072831 | A | 8/2017 | |
| CN | 107072840 | A | 8/2017 | |
| CN | 108738306 | A | 11/2018 | |
| CN | 109790663 | A | 5/2019 | |
| WO | WO-2016040105 | A1 * | 3/2016 | ....... A61F 13/15707 |
| WO | WO-2016189914 | A1 * | 12/2016 | ........... A61F 13/472 |
| WO | 2019071455 | A1 | 4/2019 | |

OTHER PUBLICATIONS

International Search Report and Written Opinion; Application Ser. No. PCT/CN2020/074093; dated Nov. 3, 2020, 11 pages.
PCT Supplementary Search Report and Written Opinion for PCT/CN2020/074093 dated Jun. 23, 2022, 8 pages.

* cited by examiner

APERTURED NONWOVEN WEB AND METHOD OF FORMING THE SAME

CROSS REFERENCE TO RELATED APPLICATION

This application is a continuation, under 35 U.S.C. § 120, of Patent Application No. PCT/CN2020/074093, filed on Jan. 31, 2020, the entire disclosure of which is hereby incorporated by reference herein in its entirety.

FIELD OF THE INVENTION

The present invention relates to nonwoven webs suitable for use in absorbent articles, and methods of forming such webs. Examples relate in particular to carded, through air bonded nonwoven webs, with apertures, suitable for use in the topsheet or backsheet of an absorbent article.

BACKGROUND OF THE INVENTION

Absorbent articles, such as diapers, pants, adult incontinence pads, sanitary napkins and pantiliners, typically comprise a topsheet and a backsheet, with an absorbent core disposed between the topsheet and the backsheet. The topsheet and/or backsheet (and optionally other layers of the absorbent article) may comprise or consist of nonwoven webs.

It is desirable that nonwoven webs for use in absorbent articles are able to withstand the processing conditions in typical converting processes used in the manufacture of the absorbent articles. At the same time, it is important that the nonwoven webs are able to perform their functions adequately in the finished absorbent article. In some cases, the functional requirements placed on the nonwoven webs may come into conflict with the factors that would help them to be more robust to the converting processes.

The outer surface of a topsheet is desirably soft, for example, since it comes into contact with the skin of the wearer. The outer surface of a backsheet may also be provided by a nonwoven material. This can help to improve the perception of softness of the article. It may also help to create the impression of an article that is more like the woven fabric of an undergarment (compared with an article that has an exposed polymer film at the outer surface of the backsheet). Accordingly, a nonwoven for providing the outer surface of a backsheet is desirably also soft.

Unfortunately, softness of a nonwoven may be correlated with poor tensile properties. A very soft nonwoven may be more inclined to exhibit negative behaviors such as breaking, folding, necking, or wrinkling, during conversion to an absorbent article.

There is a need for improved nonwoven materials, which are robust to converting processes used in the manufacture of absorbent articles, and are themselves economical to manufacture, without compromising on the functional performance of either the nonwoven or the absorbent article as a whole, when in use.

SUMMARY OF THE INVENTION

The invention is defined by the claims. According to one aspect, there is disclosed a nonwoven web suitable for use in a disposable absorbent article wherein the nonwoven web has a first surface and a second surface opposing the first surface and includes a plurality of apertures, each apertures being defined by an opening in the first surface and a side wall, wherein the side walls of the apertures have a mean height of less than about 460 µm, and a Fiber Segment Orientation Index of the nonwoven web is less than 0.46.

According to another aspect, there is disclosed is a method of producing a nonwoven web with apertures, the nonwoven web having a first surface and a second surface and being suitable for use in a disposable absorbent article, the method comprising: providing a precursor web; providing a pair of rolls comprising a male roll and a female roll, the male and female rolls defining a nip between them, the female roll having an external surface comprising a plurality of recesses, the male roll having an external surface comprising a plurality of pins, wherein the pins are configured to mate with the recesses in the vicinity of the nip as the male roll and the female roll rotate; feeding the precursor web to the pair of rolls at a feed rate; using the nip between the pair of rolls, creating apertures in the precursor web to thereby produce the nonwoven web, each apertures being defined by an opening in the first surface and a side wall; and taking the nonwoven web off the pair of rolls at a take-off rate, wherein the feed rate is different from the take-off rate, and the take-off rate divided by the feed rate defines a drawing ratio of at least 1.06, and the side walls of the apertures have a mean height of less than 460 µm.

Also disclosed is the use of a method as claimed and/or as summarized above, to produce a nonwoven as claimed and/or as summarized above.

According to another aspect, there is disclosed an absorbent article comprising: a topsheet; a backsheet; and an absorbent core between the topsheet and the backsheet, wherein at least one of the topsheet and the backsheet comprises a nonwoven web as claimed and/or as summarized above.

The article is illustrated in the Figures as a taped diaper. For ease of discussion, the absorbent article and the acquisition-distribution system will be discussed with reference to the numerals referred to in these Figures. The Figures and detailed description should however not be considered limiting the scope of the claims, unless explicitly indicated otherwise. In particular, the invention may also be used in a wide variety of absorbent article forms, such as pant type diapers, which are pre-formed and are worn like an underwear garment, or female protection sanitary pads.

It will be understood that all of the features, values, and ranges disclosed above and in the claims are intended to be combined in any combination.

BRIEF DESCRIPTION OF THE DRAWINGS

The invention will now be described by way of example with reference to the accompanying drawings, in which.

Figure 1:
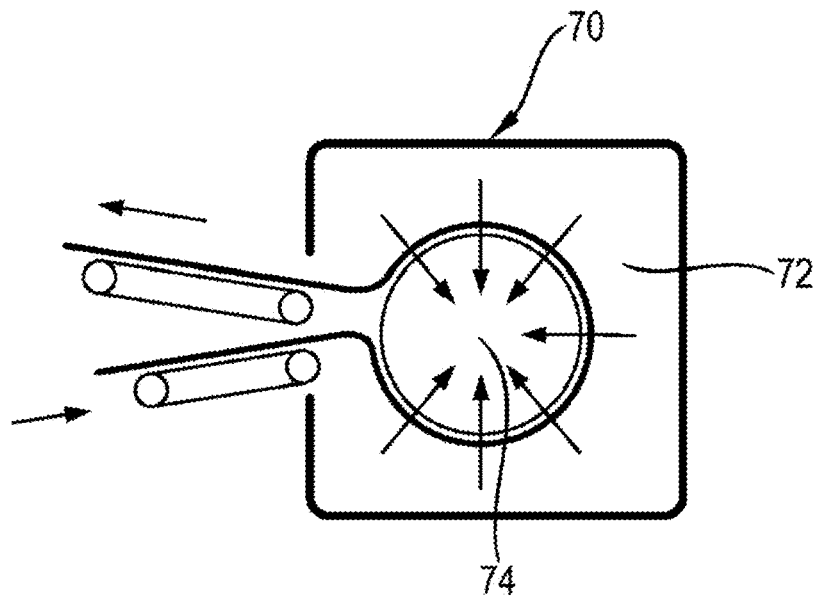
FIG. 1 is a schematic drawing illustrating a through air bonding process.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION OF THE INVENTION

The following description will focus primarily on examples of nonwoven webs for use as or in the topsheets of absorbent articles, such as diapers or pants. However, this is merely exemplary and it will be understood that these nonwovens are also suitable for use in other contexts. Similarly, it will be understood that variants of the disclosed examples are suitable for use both as topsheets and other components in absorbent articles.

Overview

Nonwoven materials, in particular, an apertured nonwoven material can be used as a component of absorbent articles such as a topsheet or an outer cover. The use of apertures can contribute to improved fluid handling properties (for example acquisition of insults) as well as enhancing the perception that the absorbent article has good absorption properties.

However, it has been found that failures, such as wrinkling, can occur on the converting line when using nonwoven materials. Without wishing to be bound by theory, it is believed that the wrinkles are caused by "bump ups" of the material in the thickness direction (z-direction) when tension is applied along the MD direction in the converting direction. In other words, the neckdown fibers tend to pack densely in the thickness direction to cause bump ups. As a result, when the material is twisted on converting idlers, the bump ups have a tendency to fold together. Such failures are more serious when using carded nonwoven such as carded TAB nonwovens which are preferred as they can contribute to softness and perceived softness.

It has also been found that the wrinkling failures can be reduced or avoided by increasing the tensile modulus of the nonwoven material. In principle, the modulus could be increased either by increasing the number of fibers in the nonwoven or by enhancing fiber bonding conditions.

The number of fibers in a unit sample of nonwoven material is influenced by the fiber denier and basis weight. To increase the number of fibers, either the fiber denier can be reduced, or the basis weight can be increased, or both. However, increasing the basis weight generally increases cost. Meanwhile, it is also desirable that the topsheet feels dry to the wearer of the absorbent article. Increasing the basis weight and/or reducing the fiber denier will tend to increase water retention in the topsheet, leading to a topsheet that feels wetter.

Furthermore, any attempt to change the fiber bonding conditions in order to increase the tensile modulus may have other negative consequences. For example, if the temperature of the through air bonding process is increased, the nonwoven may become more brittle.

It would be desirable to increase the tensile modulus of the nonwoven material, without changing the basis weight, fiber denier, or bonding conditions.

It has surprisingly been found that the tensile modulus may be enhanced without changing the basis weight, fiber denier, or bonding conditions, by controlling the distribution of fiber segment orientation in the nonwoven material. The orientation of fiber segments can differ from the orientation of the fibers. The orientation of a fiber may be defined as the orientation of a vector joining the ends of the fiber. If the fiber were straight, all of the segments of the fiber would share the same orientation as the whole fiber. However, fibers are typically not straight. In particular, staple fibers for making through air bonded nonwoven materials generally have a certain crimp. Thus, even if all of the fibers were oriented along the machine direction (MD), not all of the fiber segments would be oriented in this direction.

Definitions

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable pants.

As used herein, the terms "autogenously bonding", "autogenously bonded" and "autogenous bond" refer to bonding between discrete fibers of a carded nonwoven web using through-air bonding. Autogenous bonding does not apply solid contact pressure such as is applied for point-bonding or calendaring processes and is done independently of externally added additives which promote or facilitate bonding, such as adhesives, solvents, and the like.

As used herein, "bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core/sheath subsections, side-by-side subsections, radial subsections, etc.

Any preferred or example embodiments described below are not limiting the scope of the claims, unless specifically indicated to do so. The words "typically", "normally", "advantageously" and the like also qualify features that are not intended to limit the scope of the claims unless specifically indicated to do so.

As used herein, the term "cross-machine direction" (or CD) is the direction perpendicular to the machine direction (or MD).

As used herein, "disposable" is used in its ordinary sense to mean an article that is disposed of or discarded after a limited number of usages over varying lengths of time, for example, fewer than 20 usages, fewer than 10 usages, fewer than 5 usages, or fewer than 2 usages. If the disposable absorbent article is a diaper, a pant, sanitary napkin, sanitary pad or wet wipe for personal hygiene use, the disposable absorbent article is most often intended to be disposed of after single use.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant maybe preformed anywhere along the circumference of the article (e.g., side fastened, front waist fastened). In a diaper, the waist opening and leg openings are only formed when the diaper is applied onto a wearer by (releasably) attaching the longitudinal edges of the first and second waist region to each other on both sides by a suitable fastening system.

As used herein, "fiber segment" refers to a longitudinal segment of a fiber, the segment having of length 0.1 mm. There are thus 10 such fiber segments per mm of fiber length. The total number of fiber segments in a fiber is 10 times the length of the fiber in mm.

As used herein, the term "machine direction" (or MD) is the direction parallel to the flow of a material through a manufacturing line.

As used herein, "monocomponent" refers to fiber formed of a single polymer component or single blend of polymer components, as distinguished from Bicomponent or Multicomponent fiber.

As used herein, "multicomponent" refers to fiber having a cross-section comprising two or more discrete polymer components, two or more discrete blends of polymer components, or at least one discrete polymer component and at least one discrete blend of polymer components. "Multicomponent fiber" includes, but is not limited to, "bicomponent fiber."

As used herein, the term "non-consolidated fibers" refers to fibers which are not formed into a self-sustaining, integral web.

As used herein, a "nonwoven web" is a manufactured web of directionally or randomly oriented fibers, consolidated and bonded together. The term does not include fabrics that are woven, knitted, or stitch-bonded with yarns or filaments. The basis weight of nonwoven webs is usually expressed in grams per square meter ($g/m^2$).

The term "web" as used herein means a material capable of being wound into a roll. Webs include but are not limited to nonwovens.

Unless otherwise specified, all dimensions and measurements specified herein are understood to be measured using the corresponding experimental procedures described in the "Test Methods" section of this document.

Nonwoven Web

The nonwoven of the present invention comprises a plurality of apertures, each of apertures having a side wall. The side walls of the apertures have a mean height of less than about 460 μm, or less than about 450 μm, or less than about 440 μm. The nonwoven has a Fiber Segment Orientation Index of the nonwoven web may be less than about 0.46, or a less than about 0.45, or less than about 0.44. The Fiber Segment Orientation Index of the nonwoven web may be less than about 0.41, or less than about 0.35. The Fiber Segment Orientation Index of the nonwoven web may be at least 0.05, optionally at least 0.1, 0.15, or 0.2.

The inventors have found that a value of the Fiber Segment Orientation Index (FSOI) in the range mentioned above provides the nonwoven with greater tensile strength than a comparable nonwoven having a larger value of FSOI. It may provide the nonwoven with a tensile strength that is sufficient for typical converting processes applied in the manufacture of disposable absorbent articles. For example, it may provide the nonwoven with a tensile strength that is sufficient to reduce or avoid necking, wrinkling, and folding on converting rolls.

It is assumed that the nonwoven web has a substantially uniform FSOI value. That is, any 5 mm×5 mm sample of the nonwoven web, including at least one complete aperture, has substantially the same FSOI value.

Without wishing to be bound by theory, it, it is believed that providing aperture-side-walls with an appropriately selected height, and drawing the nonwoven with an appropriate drawing ratio, may contribute to orienting the segments of the fibers in the web. In particular, it contributes to orienting the fiber-segments in the machine direction. The inventors have found that this provides a beneficial effect in terms of tensile strength, with an associated improvement in the robustness of the nonwoven web to typical converting processes used in the production of disposable absorbent products.

The nonwoven web may have a tensile modulus in the machine direction, at 4% strain, of at least 30 N/cm, optionally at least 33 N/cm, optionally at least 35 N/cm, and optionally 35 N/cm. The nonwoven web may have a tensile modulus in the machine direction, at 4% strain, of at most 50 N/cm, optionally at most 40 N/cm, optionally at most 38 N/cm.

The nonwoven web may have a basis weight in the range 10 to 60 $g/m^2$, or 20 to 40 $g/m^2$, or 30 to 40 $g/m^2$, or 35 $g/m^2$.

The nonwoven web may have a total open area percentage in the range 5% to 25%, or 8% to 21%, or 8% to 14%.

The nonwoven web comprises greater than 50% by weight of the web of thermoplastic fibers. The nonwoven web may comprise at least 60% by weight of the web of the thermoplastic fibers, optionally at least 70%, 80%, 90%, or 95% by weight of the web, further optionally the nonwoven web consisting essentially of the thermoplastic fibers.

Such an apertured nonwoven web of thermoplastic fibers may be useful in a variety of components of an absorbent article—including but not limited to components where softness is desirable, such as those components on an external surface of the absorbent article.

The nonwoven web may be a through air bonded nonwoven web.

In some embodiments, the nonwoven web is a carded nonwoven web such as carded through-air bonding nonwoven. The carded nonwoven web may comprise at least 50%, by weight of the nonwoven web, of staple fibers. In the presently described example, the nonwoven web comprises at least 95% by weight of the web of staple fibers, and preferably consists essentially of the staple fibers. The carded nonwoven web may, in addition to the staple fibers, consist of minor amounts of additives, such as odor control additives, perfumes, colored pigments or the like.

Staple fibers are short fibers. In the present example, the staple fibers have a mean length of 38 mm. The staple fibers are of substantially uniform length. It has been found that if the staple fibers are too short, they may detach from the cylinder during carding. On the other hand, if the staple fibers are too long, it may be difficult to transfer them off the cylinder.

The staple fibers laid down by the carding process form a layer of non-consolidated fibers. The layer then undergoes a through-air bonding process to form an autogenously bonded web. In the present example, the basis weight of the carded nonwoven web is 35 g/m$^2$.

Through Air Bonding

As used herein, through-air bonding or "TAB" (also known as air through bonding or "ATB") means a process of bonding staple fibers of a layer of non-consolidated fibers, in which air is forced through the web, wherein the air is sufficiently hot to melt (or at least partly melt, or melt to a state where the fiber surface becomes sufficiently tacky) the polymer of a staple fiber or, if the staple fibers are multicomponent fibers, wherein the air is sufficiently hot to melt (or at least partly melt, or melt to a state where the fiber surface becomes sufficiently tacky) one of the polymers of which the fibers of the web are made. The air velocity is typically between 30 and 90 meter per minute and the dwell time may be as long as 6 seconds. The melting and resolidification of the polymer provides the bonding between different staple fibers.

A through air bonder is schematically shown in FIG. 1. In the through-air bonder 70, air having a temperature above the melting temperature of the polymer of the staple fiber or, if the staple fibers are multicomponent fibers, above the melting temperature of a first fiber component and below the melting temperature of a second fiber component, is directed from the hood 72, through the web, and into the perforated roller 74. Alternatively, the through-air bonder maybe a flat arrangement wherein the air is directed vertically downward onto the web. The operating conditions of the two configurations are similar, the primary difference being the geometry of the web during bonding.

The hot air melts at least part of the fibers to consolidate and integrate the layer of fibers into a web.

It should be understood that the parameters of the through-air bonder depend on factors such as the type of polymers used and thickness of the fibrous layer.

Fibers

As mentioned above, the nonwoven web of the present invention comprises at least 50%, by weight of the nonwoven web, of thermoplastic fibers.

The thermoplastic fibers may have a linear density in the range 0.6 to 6.6 dtex, or 1.3 to 4.5 dtex, or 2.2 to 4.5 dtex.

Thermoplastic fibers useful for the nonwoven web according to the present disclosure include monocomponent fibers as well as multicomponent fibers. Multicomponent fibers are especially useful. Suitable multicomponent fibers are bicomponent fibers, such as core/sheath bicomponent fibers and side-by-side bicomponent fibers. The core/sheath bicomponent fibers maybe concentric or eccentric fibers.

The monocomponent or multicomponent fibers may be made of polymeric materials, such as polyolefins (e.g. polypropylene, or polyethylene), polyester, polyethylene terephthalate (PET), CoPET, polybutylene terephthalate, polyamide, polylactic acid, viscose, and combinations thereof. The polymers may also comprise copolymers such as Co-PET. If the fibers comprise core/sheath bicomponent fibers, it is desirable that the sheath is made of a polymer which has a melting point below the melting point of the polymer which forms the core. If side-by-side bicomponent fibers are used, the polymers forming the first and second component may also have different melting points. If such bicomponent fibers are subjected to through-air bonding, the temperature of the through air bonding process is selected such that the polymer of the component having the lower melting point is molten is at least partially transferred to a molten state (or to a state where the fiber surface becomes sufficiently tacky) such that the fibers bond together while the polymer of the component having the higher melting point remains substantially unaffected.

The nonwoven web of the present invention may comprise a mixture of different types of fibers, such as a mixture of monocomponent fibers and bicomponent fibers.

In some embodiments, the thermoplastic fibers may be staple fibers. The thermoplastic fibers may have a mean length in the range 20 to 80 mm, optionally 30 to 60 mm, optionally 38 to 51 mm, and optionally 38 mm. The thermoplastic fibers may be substantially uniform in length. The fibers may have a standard deviation of fiber-length of less than 20 mm, optionally less than 10 mm, optionally less than 5 mm. In some embodiments, the staple fibers may be crimped multicomponent staple fibers, optionally crimped bicomponent staple fibers. The staple fibers may have a crimp number in the range 13 to 17 per 2.5 cm (13 to 17 per inch). The crimped staple fibers may be a bicomponent fiber having a core-sheath arrangement, optionally comprising a core formed of polyethylene terephthalate, and a sheath formed of polyethylene. In some examples, a certain percentage of non-crimped fibers can be blended with the crimped fibers; however, a high level of non-crimped fibers may cause process failures, such as cylinder blocking. The nonwoven web may comprise at least 95% by weight of the nonwoven web of crimped fibers. In one embodiment, the fibers have a crimp number in the range 13 to 17 per 2.5 cm (13 to 17 per inch).

Apertures

Figure 2:
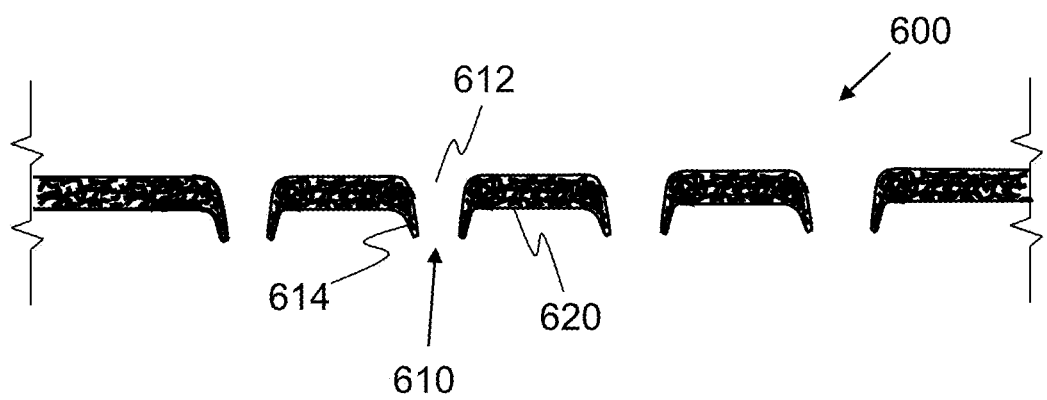
FIG. 2 is a diagram illustrating apertures in a nonwoven.

As illustrated in FIG. 2, the nonwoven 600 comprises a plurality of apertures 610 extending through the nonwoven 600. The plurality of apertures 610 may be uniformly distributed on the nonwoven 600. To ensure material stability, the smallest distance between the majority of the apertures regardless of their particular shape and size is preferably at least 0.3 mm, preferably at least 1.0 mm. This distance is measured center-to-center on the second surface of nonwoven 600. The apertures are separated by "land" area 620, which is preferably substantially flat—that is, lying substantially in the x-y plane of the nonwoven web.

The apertures 610 may extend inwardly, toward the absorbent core, for example when the nonwoven 600 is disposed on the wearer-facing side of the article, or when the nonwoven 600 is disposed on the garment-facing side of the article.

The side walls 614 of the apertures (also referred to herein as the "skirts" of the apertures) may extend at least 0.01 mm beyond the second surface of the nonwoven 600, preferably at least 0.1 mm, 0.2 mm, or 0.3 mm beyond the first surface of the nonwoven 600. The apertures may be tapered and take a conical shape such that the x-y dimensions of the aperture are larger at the opening 612 in the first surface than at the distal edge of the side wall 614.

The mean height of the side walls of the apertures may be less than 440 µm, optionally less than 390 µm, optionally less than 360 µm. The mean height of the side walls of the apertures may be at least 10 µm, optionally at least 50 µm, 100 µm, 200 µm, or 300 µm. The side walls of the apertures may be substantially uniform in height. The side walls of the apertures may have a standard deviation about the mean height of less than 40 µm. Optionally, the side walls of the apertures in a given nonwoven web may be within a range +/−40 µm of the mean height.

The apertures may have a mean area per aperture in the range 0.2 to 4 mm$^2$, optionally 0.5 to 2.4 mm$^2$, optionally 0.5 to 1.0 mm$^2$. The standard deviation of the area per aperture may be less than 2 mm$^2$, optionally less than 1 mm$^2$, optionally less than 0.5 mm$^2$, optionally less than 0.2 mm$^2$.

The apertures may be substantially uniformly distributed over the nonwoven web, such that any sample of the web having an area of 35 mm×20 mm has substantially the same total open area percentage as any other such area.

In some embodiments, the apertures may be circular or elliptical.

The apertures in a given nonwoven web may have a substantially uniform size (area) and/or shape.

The apertures may vary in shape. For example, the (plan-view) shape of the apertures as seen from the first or second surface of the nonwoven 600 may be circular, elliptic, rectangular or polygonal. Preferably, the apertures have a circular shape, an elliptic shape or a polygonal shape. The apertures may be three-dimensional. The three-dimensional shape of the apertures may be cylindrical (e.g. with a circular or elliptic base), prismatic (e.g. with a polygonal base), truncated cone or pyramidal.

The apertures may vary in size between different nonwoven webs. When the nonwoven web is used as a component of an absorbent article such as a topsheet, nonwovens with apertures generally have an increased risk of rewet, i.e. of liquid passing back from components underneath the topsheet (such as the absorbent core) into and through the topsheet. Smaller apertures can contribute to lower rewet and generally tend to create less red marking on the skin of the wearer. Hence, the apertures may have a mean size of 4 mm$^2$ or less, of 3.5 mm$^2$ or less, of 3.0 mm$^2$ or less, or of 2.4 mm$^2$ or less. The size of the apertures may be at least 0.2 mm$^2$, optionally at least 0.5 mm$^2$. The size is determined on the first side of the nonwoven, and for example for conical apertures the larger aperture opening is determined.

Figure 3:
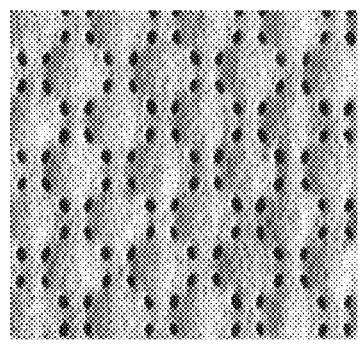
FIG. 3 is an image of an apertured nonwoven web according to an example.
Figure 4:
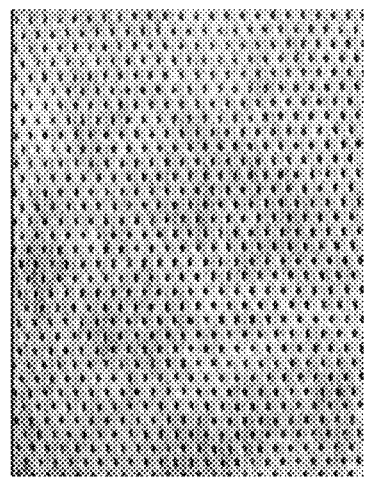
FIG. 4 is an image of an alternative pattern of apertures for a nonwoven web.

Various different patterns of apertures may be used. In the presently described example, the pattern is as shown in FIG. 3. An alternative pattern is shown in FIG. 4.

The pattern of apertures used in the present example (FIG. 3) produced a nonwoven web having a total open area percentage in the range 8% to 14% (depending on the process parameters). The mean area per aperture may be in the range 0.5 mm$^2$ to 2.4 mm$^2$. The apertures may be substantially uniform in size. The standard deviation of the area per aperture is 0.07 mm$^2$. The aperture areas were found to vary +/−0.15 mm$^2$ about the mean value.

The alternative pattern of apertures (FIG. 4) results in the nonwoven web having a total open area percentage in the range 17% to 21%. The mean area per aperture is 0.53 mm$^2$. The standard deviation is 0.05 mm$^2$.

Process

Figure 5:
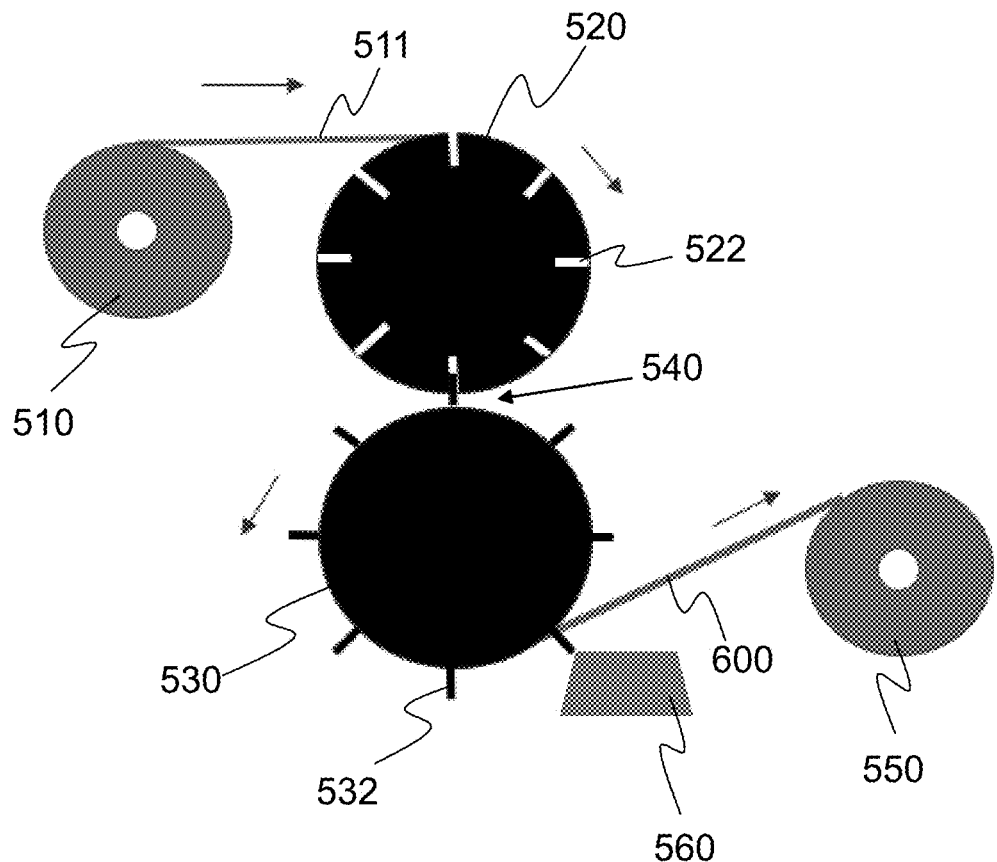
FIG. 5 schematically illustrates a process for forming an apertured nonwoven.

A method of producing an apertured nonwoven web of the present invention will be described with reference to FIG. 5. This drawing illustrates an example apparatus and process for forming an apertured web. The apparatus comprises a feed roll 510; a pair of rolls comprising a female roll 520 and a male roll 530; and an optional take-off roll 550. A nip 540 is defined between the female roll 520 and the male roll 530. At least one of the male roll 530 and female roll 520 may be heated. The male roll 530 may be heated to a higher temperature than the female roll. In some embodiments, the male roll may be heated to a temperature in the range 133° C. to 146° C.; and the female roll may be heated to a temperature in the range 108° C. to 136° C. An optional cooler 560 is provided, for cooling the nonwoven web between the male roll 530 and the take-off roll 550 for cooling the apertured web after it is taken off the pair of rolls.

The male roll 530 having an external surface comprises a plurality of pins 532. The female roll 520 having an external surface comprises a plurality of recesses 522 such as grooves and holes. In one embodiment, the forming elements 532 are all identical to one another. Likewise, the recesses 522 may be all identical to one another. All the pins on the male roll preferably have a circular cone shape, with base diameter in the range 1.8 to 2.5 mm, and height in the range 2.0 to 3.5 mm. The side surfaces of the cone-shaped pins are polished to be very smooth. When the recesses on the female roll are holes, they may have a similar circular cone shape to the pins, but the diameter and depth may be 0.1 to 0.5 mm larger than the diameter and height, respectively, of the pins.

Together, the female roll 520 and male roll 530 form an aperturing unit. A plurality of pins 532 are provided on the surface of the male roll 530. A corresponding plurality of recesses 522 are provided in the surface of the female roll 520. The rolls 520, 530 are arranged such that each pin 532 engages with a respective recess 522 in the vicinity of the nip 540, as the rolls 502, 530 rotate. As pictured in the drawing, the female roll 520 is arranged to rotate clockwise and the male roll 530 is arranged to rotate anticlockwise, or vice versa. The pattern of the pins and recesses on the pair of rolls corresponds to the pattern of the apertures in the nonwoven (and vice versa).

During operation, precursor web 511 is unwound from the feed roll 510, and fed to the female roll 520 at a feed rate. The precursor web travels around the female roll 520 to the nip 540. In the nip 540, the nonwoven precursor web is compressed between the rolls 520, 530. As pictured in the drawing, the web travels through the nip where the engagement between the pins and holes creates apertures in the web. The fibers are pushed around the pins to form the apertures. Each apertures is defined by an opening in the first surface of the web (the surface facing the male roll 530) and a skirt (side wall). The side wall may project from the second surface of the web (the surface facing the female roll 520). The height of the side walls can be controlled by adjusting the engagement between the pins and the respective recesses (which, in turn, is determined by the spacing between the male roll and the female roll).

The spacing between the rolls 520, 530 is adjustable, to vary the depth of engagement of the pins in the recesses. In order to increase the height of the side walls, the rolls can be moved incrementally closer together, to increase the depth of engagement. To decrease the height of the side walls, the rolls can be moved incrementally further apart, to decrease the depth of engagement.

By creating the apertures, the pair of rolls 520, 530 produce the apertured nonwoven web 600. The web 600 travels around the male roll 530 until it reaches a take-off location. It is taken off the male roll 530, from the take-off location, to the take-off the roll 550. This is done at a take-off rate. The cooler 560 is provided at the takeoff location. The apertured nonwoven web 600 may be wound onto the take-off roll 550.

The rolls 520, 530 are preferably heated. In the presently described example, the male roll is heated to a temperature in the range 133° C. to 146° C.; and the female roll is heated to a temperature in the range 108° C. to 136° C. In this example, as already described above, the fibers are 2.2 dtex (2 denier) PET/PE core/sheath bicomponent staple fibers. The speed of the web at the nip between the rolls is approximately 60 m/min. As will be appreciated by those skilled in the art, the temperatures of the rolls may be selected depending upon the composition of the precursor web to be processed, the speed of the rolls, and the ambient temperature.

Figure 6:
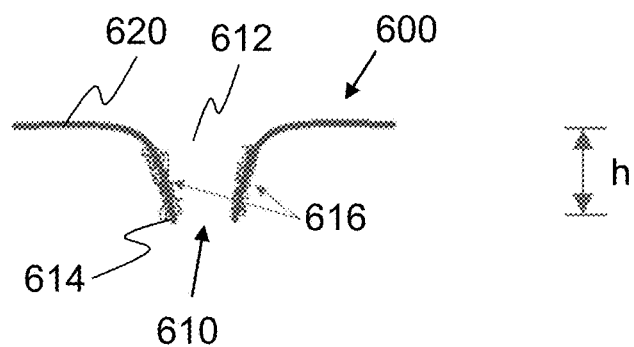
FIG. 6 is a simplified schematic drawing showing a cross-section through an aperture in an apertured nonwoven web.

An exemplary aperture is illustrated in a simplified schematic drawing in FIG. 6. The apertured nonwoven web 600 comprises a plurality of apertures 610, with land areas 620 between the apertures. Each aperture 610 is defined by an opening 612 in the first surface of the web (the upward-facing surface in FIG. 6) and a side wall 614 projecting from the second surface (the downward-facing surface in FIG. 6). The aperture side wall 614 has a height, h, as shown. Also shown schematically are individual fibers 616 in the aperture side wall 614.

As mentioned above, the precursor web 511 is fed to the female roll 520 by the feed roll 510 at a feed rate. The apertured nonwoven web 600 is taken off the male roll 530 by the take-off roll 550 at a take-off rate. The take-off rate is greater than the feed rate. The take-off rate divided by the feed rate defines a drawing ratio. The drawing ratio may be at least about 1.06, or at least about 1.08. The drawing ratio may be at most 1.2, optionally at most 1.15. It has been found that a drawing ratio of at least 1.06, in combination with aperture side walls having a mean height of less than about 460 μm, or less than about 450 μm, or less than about 440 μm, produces a beneficial effect on fiber segment orientation, such that the machine direction tensile modulus of the apertured nonwoven web 600 is increased, relative to comparable webs with different drawing ratios and side wall heights. Further increasing the drawing ratio—for example, to at least 1.08—while further reducing the aperture side wall height—for example, to less than 360 μm—was found to further enhance the machine direction tensile modulus.

Without wishing to be bound by theory, it is believed that the material transformation may be explained as follows. A drawing ratio of greater than one implies that the material is stretched to some extent during the aperturing process. It is believed that the nonwoven fibers are straightened, reducing or removing their crimp, during this process, so that a majority of the fiber segments are oriented along the stretching direction. However, the material modulus would not be increased by stretching alone, because when the tension was released, the nonwoven fibers would "bounce back" to their original crimped state. It is by forming the aperture structure that the straightened fiber morphology is fixed in the processed nonwoven. It has been found that when the aperture side wall height is lower than a certain value, the apertures can fix this straightened fiber morphology to increase material modulus. Heating the pair of rolls of the aperturing unit is believed to soften the staple fibers and thereby facilitate deformation. When the fibers are cooled again the fiber morphology is fixed.

The area of the apertures (in the x-y plane of the nonwoven web) is influenced by the size of the pins 532 and holes 522. The side wall height of the apertures is influenced by the depth of engagement of the pins 532 and holes 522. The shape of the apertures may be influenced by the drawing ratio. At higher drawing ratios, the apertures may become more elongated in the machine direction.

In some embodiments, a precursor web is produced separately, wound into a roll, and provided as a precursor web by unwinding the precursor web from the roll.

In other embodiments, a method of producing an apertured nonwoven web of the present invention may be carried out as a continuous process comprising producing a nonwoven precursor web and continuously aperturing the precursor nonwoven web as described above. A nonwoven precursor web can be produced by nonwoven production process well known in the industry.

EXAMPLES

Various combinations of aperture side wall height and drawing ratio were tested. The results are presented in Table 1 below. The nonwoven webs were formed as described above:

Fiber type: bicomponent core/sheath (PET/PE) staple fibers
Fiber cross section: circular
Fiber diameter: 22 μm
Fiber linear density: 4.4 dtex (4 denier)
Staple fiber length: 38 mm
Crimp no. 13-17 per 2.5 cm (13-17 per inch)
Basis weight: 35 g/m$^2$
Male roll temp.: 133° C. to 146° C.
Female roll temp.: 108° C. to 136° C.
Aperture pattern: see FIG. 3
Open area %: 10.5%
Hole area: 1.6 mm$^2$

TABLE 1

| | Aperturing conditions | | | | Topsheet |
|---|---|---|---|---|---|
| | Aperture Side wall height (μm) | Drawing ratio | Fiber Segment Orientation Index | MD tensile modulus (N/cm) | wrinkles on converting line? |
| A | 580 | 1.04 | — | 23.0 | Yes |
| B | 580 | 1.05 | 0.761 | 26.9 | Yes |
| C | 490 | 1.04 | — | 23.3 | Yes |
| D | 490 | 1.06 | 0.479 | 24.5 | Yes |
| E | 430 | 1.05 | — | 25.4 | Yes |
| F | 430 | 1.06 | 0.404 | 30.9 | No |
| G | 430 | 1.08 | 0.331 | 30.8 | No |
| H | 350 | 1.08 | 0.232 | 35.2 | No |

From the table, it can be seen that samples A-E have low tensile modulus and generate wrinkles during converting. Meanwhile, samples F-H have increased modulus and no wrinkles during converting. The wrinkling was assessed visually according to the test method described below. Reduced fiber segment orientation index correlates with increased tensile modulus. The lower the FSOI value, the more the fiber segments are preferentially aligned with the machine direction. The larger the FSOI value, the more isotropic the distribution of fiber segments in the x-y plane of the nonwoven.

Absorbent Articles

Figure 7:
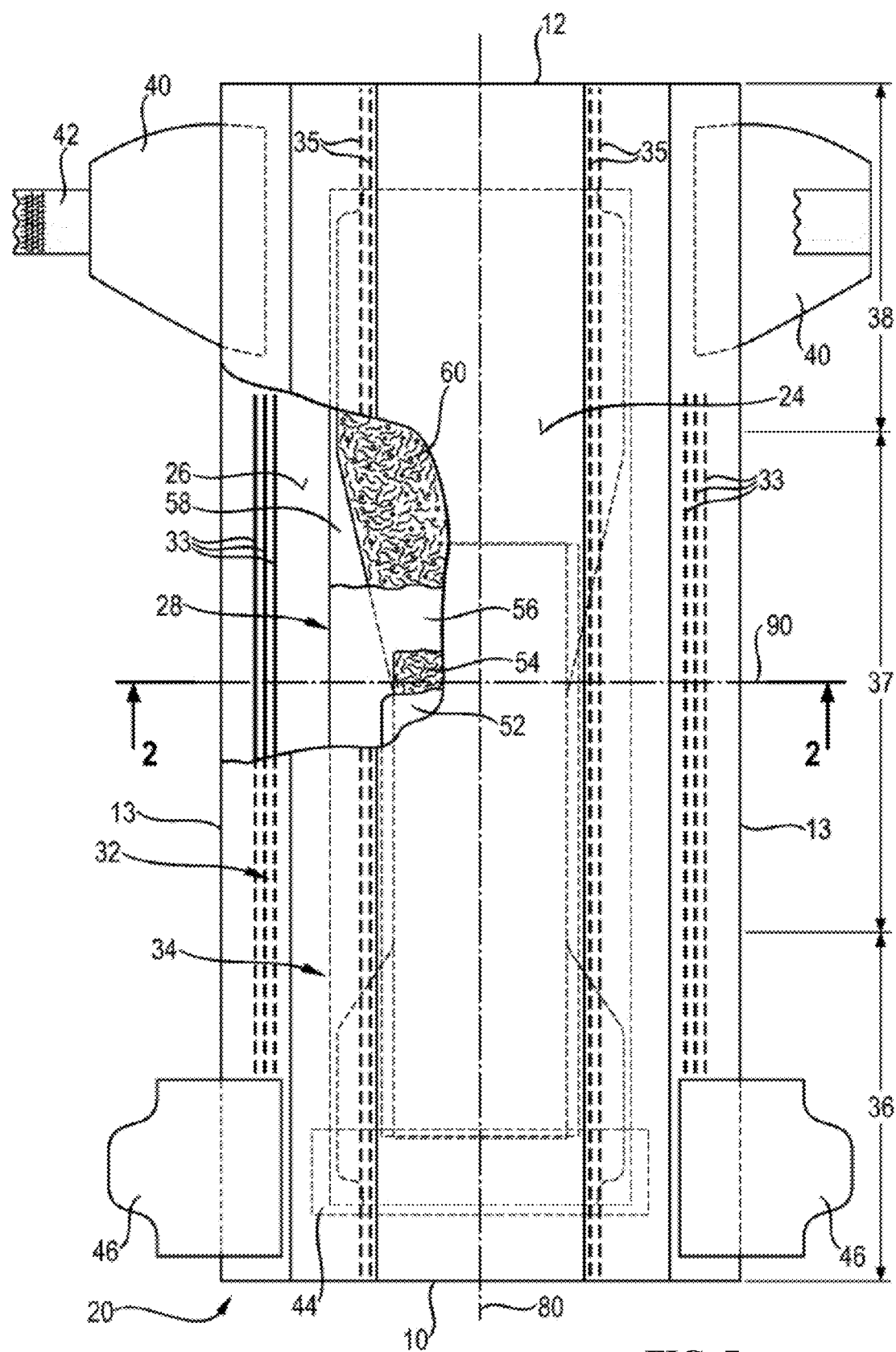
FIG. 7 is a schematic top plan view of a diaper.
Figure 8:
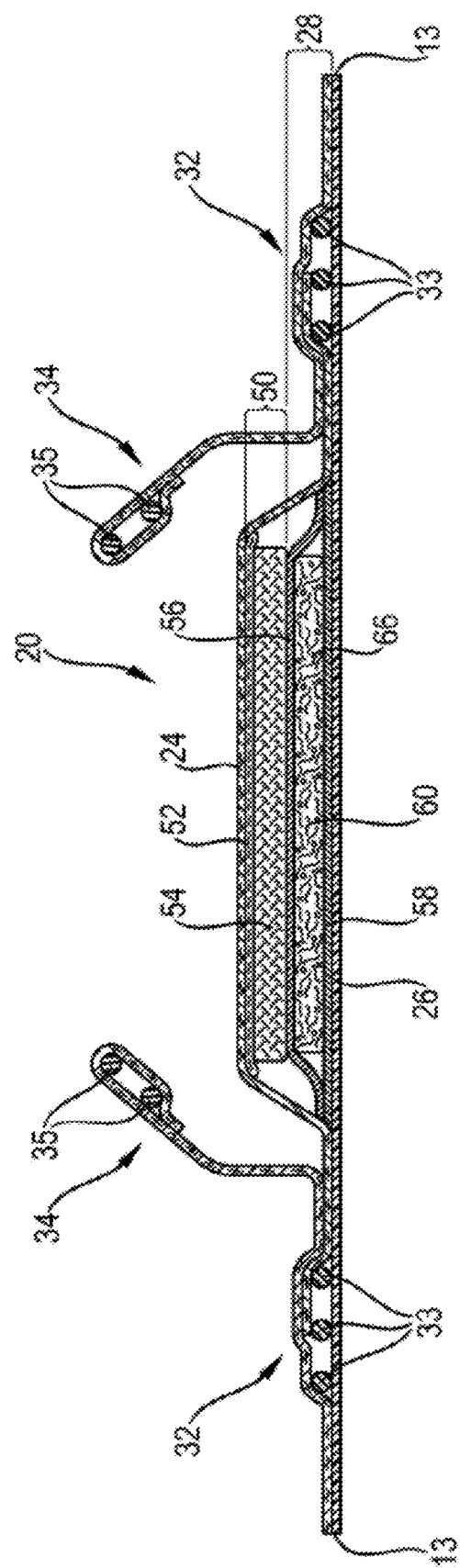
FIG. 8 is a schematic cross-sectional view of the diaper of FIG. 7, along the line 2-2.

Referring to FIGS. 7 and 8, an example absorbent article 20 is described. FIG. 7 is a top plan view of the absorbent articles 20 (shown here: a diaper), in a flat-out state, with portions of the structure being cut-away to more clearly show the construction of the absorbent article 20. The absorbent article 20 is shown for illustrative purposes only as the present disclosure may be used for making a wide variety of diapers or other absorbent articles.

The absorbent article 20 comprises a liquid permeable topsheet 24, a liquid impermeable backsheet 26, an absorbent core 28 positioned intermediate the topsheet 24 and the backsheet 26, an optional acquisition layer 52 underneath the topsheet, and, optionally, a distribution layer 54 beneath the acquisition layer and above the absorbent core. The absorbent article 20 comprises a front waist edge 10 (in a pantiliner or sanitary napkin, this edge of the article would be referred to as a front edge instead of front waist edge, given the article is considerably smaller and not worn around the waist of the wearer), and a back waist edge 12 (in a pantiliner or sanitary napkin, this edge of the article would be referred to as a back edge instead of back waist edge, given the article is considerably smaller and not worn around the waist of the wearer), and two longitudinal side edges 13. The front waist edge 10 is the edge of the absorbent article 20 that is intended to be placed towards the front of the user when worn, and the rear waist edge 12 is the opposite edge. The absorbent article 20 has a longitudinal dimension and a lateral dimension and may be notionally divided by a longitudinal axis 80 extending from the front waist edge 10 to the back waist edge 12 of the absorbent article 20 and dividing the absorbent article 20 in two substantially symmetrical halves relative to the longitudinal axis, when viewing the absorbent article 20 from the wearer-facing side in a flat, laid out configuration, as e.g. illustrated in FIG. 7.

The absorbent article 20 may be divided by a lateral axis 90 into a front half and a back half of equal length measured along the longitudinal axis 80, when the absorbent article 20 is in a flat, laid-out state. The absorbent article's lateral axis 90 is perpendicular to the longitudinal axis 80 and is placed at half the longitudinal length of the absorbent article 20.

The longitudinal dimension of the absorbent article extends substantially parallel to the longitudinal axis 80 and the lateral dimension extends substantially parallel to the lateral axis 90. The absorbent article 20 may be notionally divided into a front region 36, a back region 38 and a crotch region 37 located between the front region 36 and the back region 38 of the absorbent article 20. Each of the front, back and crotch regions are ⅓ of the longitudinal dimension of the absorbent article 20.

Absorbent articles especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet. The ADS maybe free of superabsorbent polymer.

The function of a distribution layer 54 is to spread the insulting fluid liquid over a larger surface within the article so that the absorbent capacity of the absorbent core can be more efficiently used. Distribution layers maybe made of a nonwoven material based on synthetic or cellulosic fibers and having a relatively low density. The distribution layer may typically have an average basis weight of from 30 g/m2 to 400 g/m2, in particular from 80 g/m2 to 300 g/m2.

The absorbent article 20 may further comprise an acquisition layer 52, which is provided directly beneath the topsheet and above the absorbent core (and, if present, above the distribution layer). The function of the acquisition layer 52 is to quickly acquire the fluid away from the topsheet so as to provide a good dryness for the wearer. The acquisition layer may typically be or comprise a non-woven material, for example a SMS or SMMS material, comprising a spunbonded, a melt-blown and a further spunbonded layer or alternatively a carded chemical-bonded nonwoven. The nonwoven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

A further acquisition layer may be used in addition to a first acquisition layer described above. For example a tissue layer maybe placed between the first acquisition layer and the distribution layer. The tissue may have enhanced capillarity distribution properties compared to the acquisition layer described above. The tissue and the first acquisition layer may be of the same size or maybe of different size, for example the tissue layer may extend further in the back of the absorbent article than the first acquisition layer. An example of hydrophilic tissue is a 13-15 gsm high wet strength made of cellulose fibers from supplier Havix.

The absorbent core 28 may comprise an absorbent material 60 that is a blend of cellulosic fibers (so called "airfelt") and superabsorbent polymers in particulate form encapsulated in one or more webs, see for example U.S. Pat. No. 5,151,092 to Buell. Alternatively, the absorbent core 28 may be free of airfelt, or substantially free of airfelt.

FIG. 7 also shows other typical diaper components such as a fastening system comprising fastening tabs 42 attached towards the back waist edge 12 of the absorbent article 20 and cooperating with a landing zone 44 towards the front waist edge 10 of the absorbent article 20. The absorbent article 20 may also comprise front ears 46 and back ears 40 as it is known in the art.

The absorbent article may comprise further optional other features such as leg cuffs 32 and/or barrier cuffs 34, front and/or back waist features such as front and/or elastic waistbands attached adjacent to the respective front and/or back waist edge of the absorbent article.

The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003; 5,221,274; 5,554,145; 5,569,234; 5,580,411; and 6,004,306.

In a preferred absorbent article according to an example, the topsheet 24 comprises or consists of an apertured carded through air bonded nonwoven web as described above.

(Note that the apertures in the topsheet 24 are omitted for simplicity, in the schematic drawings of FIGS. 7 and 8.) The side walls of the apertures are preferably directed inwardly, towards the absorbent core 28. The body facing surface of the absorbent article preferably comprises the first surface of the nonwoven web.

Alternatively or in addition, an apertured carded through air bonded nonwoven web as described above may be used as part of the liquid impermeable backsheet 26, or as a cover over the garment facing surface of the liquid impermeable backsheet 26. When used in this way, the garment facing surface of the absorbent article preferably comprises the nonwoven web. In particular, the garment facing surface of the absorbent article preferably comprises the first surface of the nonwoven web—that is, the side walls of the apertures are preferably directed inwardly, towards the absorbent core 28.

The diaper 20 may comprise leg cuffs 32 which provide improved containment of liquids and other body exudates. Leg cuffs 32 may also be referred to as leg bands, side flaps, barrier cuffs, or elastic cuffs. Usually, each leg cuff will comprise one or more elastic strings 33, represented in exaggerated form on FIGS. 7 and 8, comprised in the diaper for example between the topsheet and backsheet in the area of the leg openings to provide an effective seal while the diaper is in use. It is also usual for the leg cuffs to comprise "stand-up" elasticized flaps (barrier leg cuffs 34) which improve the containment of the leg regions. The barrier leg cuffs 34 will usually also comprise one or more elastic strings 35, represented in exaggerated form in FIGS. 7 and 8.

The absorbent core 28 may comprise an absorbent material 60 enclosed within a core wrap 56 and 58. The absorbent material 60 may comprise from 80% to 100% of superabsorbent polymer (SAP) 66, such as SAP particles, by total weight of the absorbent material 60. The core wrap 56 and 58 is not considered as an absorbent material 60 for the purpose of assessing the percentage of SAP in the absorbent core 28.

The absorbent core 28 of the invention may comprise adhesive for example to help immobilizing the SAP 66 within the core wrap 56 and 58 and/or to ensure integrity of the core wrap, in particular when the core wrap is made of one or more substrates. The core wrap will typically extend over a larger area than strictly needed for containing the absorbent material 60 within.

The absorbent material 60 may be encapsulated in one or more substrates. The core wrap comprises a top side 56 facing the topsheet 24 and a bottom side 58 facing the backsheet 26, as shown in FIG. 8. The core wrap may be made of a single substrate folded around the absorbent material 60. The core wrap may be made of two substrates (one mainly providing the top side and the other mainly providing the bottom side) which are attached to another. Typical configurations are the so-called C-wrap and/or sandwich wrap.

The core wrap may be formed by any materials suitable for receiving and containing the absorbent material 60. The core wrap may in particular be formed by a nonwoven web, such as a carded nonwoven, spunbond nonwoven ("S") or meltblown nonwoven ("M"), and laminates of any of these.

The absorbent article may have a wearer-facing surface and a garment-facing surface, wherein the topsheet comprises a first nonwoven web as claimed and/or as summarized above, and the wearer-facing surface of the absorbent article comprises the first surface of the first nonwoven web.

The absorbent article may have a wearer facing surface and a garment facing surface, wherein the backsheet comprises a second nonwoven web as claimed and/or as summarized above, and the garment-facing surface of the absorbent article comprises the first surface of the second nonwoven web.

Variants

Examples were given above of absorbent articles in which the topsheet and/or backsheet comprises an apertured nonwoven web. Alternatively or in addition to either (or both) of these possibilities, another component of the absorbent article may comprise the apertured nonwoven web.

Although the example was given above of a diaper, the apertured nonwoven web may be used in other absorbent articles.

Examples were given above of apertured carded through air bonded nonwoven webs. Other examples may include apertured spunbonded (S) nonwoven webs, or apertured meltblown (M) nonwoven webs. Still other examples may include composites or laminates comprising or consisting of a plurality of layers. For example, apertures may be formed in a nonwoven web formed of a plurality of spunbond and/or meltblown layers, such as an SMS nonwoven web, or an SMMS nonwoven web. Methods of making spunbond, meltblown, and S-M combined webs are known in the art. An aperturing apparatus and process may be employed as described above.

Nevertheless, it is believed that the advantageous effects described herein are particularly relevant for apertured carded through air bonded nonwoven webs formed of staple fibers.

Test Methods

Sample Preparation

When a nonwoven is available in a raw material form, a specimen for test is cut from the raw material. When a nonwoven is a component of a finished product, the nonwoven is removed from the finished product using a razor blade to excise the nonwoven from other components of the finished product to provide a nonwoven specimen. A cryogenic spray (such as Cyto-Freeze, Control Company, Houston TX) may be used to remove the nonwoven specimen from other components of the finished product, if necessary.

Tensile Modulus

This method is used to determine nonwoven tensile modulus at 4% elongation.

Apparatus: MTS Criterion™ Model 42 (MTS Systems Corporation, Eden Prairie, MN, USA), or equivalent, is employed to record the strain-stress curve of the nonwoven material. A 100-N load cell of S-beam design (such as MTS model LSB.102, or equivalent), is used.

1. Wash hands prior to preparing materials for analysis to remove dirt and oil that could affect the results.
2. If samples are received in bulk (e.g. rolls of material), remove any exposed layers of the sample roll or box to ensure that no contaminated or damaged material is measured.
3. Using scissors, cut material off the roll to be sampled. The material sample must be long enough in the MD direction to allow at least one test specimen 200 mm long to be cut for testing.

4. Condition samples at 23±2° C. (73±2° F.), 50±2% relative humidity, for a minimum of 2 hours prior to testing.
5. Using scissors or a paper cutter, cut a test specimen 200 mm long in MD direction, and 50 mm width in CD direction.
6. Calibrate MTS according to manufacturer's instructions before beginning any testing.
7. Before loading each specimen, check that the load cell reading is 0±0.005 N. Zero the instrument according to manufacturer's instructions if necessary before loading the specimen.
8. Load the test specimen on MTS force gauge, and set the initial gauge length to be 100 mm. Set the force gauge moving speed to be 100 mm/min, and moving length to be 20 mm.
9. Record the force values (Newtons) of 3.5% and 4.5% material strain. Then, the material modulus is calculated as follows:

$$\text{Tensile Modulus (4\% strain)} = \frac{F(4.5\%) - F(3.5\%)}{4.5\% - 3.5\%} \times \frac{100\%}{\text{sample width}}$$

Where F (% strain) is the force read in units of Newtons at a given strain and sample width is the width of sample in units of cm (in this case 5.0 cm).

Topsheet Wrinkle

The presence of topsheet wrinkles is evaluated by visually checking diapers manufactured using the topsheet, as follows.

Apparatus: A stretch board is constructed from a 6 mm pane of colorless, transparent acrylic or polycarbonate. Transparent hook strips are positioned and affixed to the pane so as to enable a diaper to be pulled and held tight over a span of interest. The transparent pane is positioned on a light box (such as an Art-O-Graph Light Pad (Studio Designs, Inc., Commerce, CA, USA, or equivalent)

1. Place the diaper on the stretch board and extend to 100% with topsheet side facing up.
2. Check whether the topsheet is folded/wrinkled. That is, check the stretched diapers and evaluate whether there are any 2D or 3D patterns on the nonwoven material that are not part of the product design. In particular, check for folding of different parts of the nonwoven web in the CD or MD directions.

Fiber Segment Orientation Index (FSOI)

The FSOI is a measure of fiber-segment isotropy/anisotropy. It is calculated from a computed tomography (CT) scan of a sample of the nonwoven web. The first stage in the test procedure is to obtain the CT scan.

Apparatus: X-ray scanner, such as GE Phoenix vltomeix m. (available from GE Sensing & Inspection Technologies GmbH, Niels-Bohr-Str. 7, 31515 Wunstorf, Germany), or equivalent.

A square shaped sample with area of 5 mm×5 mm is cut from the non-woven sample for X-ray CT scanning. The sample should include at least one complete aperture, so that it includes fibers in the vicinity of the aperture as well as fibers in the land area, surrounding the aperture.

The sample is then mounted on a sample holder. The sample holder is then placed in the X-ray scanner for CT data acquisition. For the CT scanning, the chosen voxel size to achieve sufficient resolution would be at least two times smaller than the fiber diameter. The scan should be free of artifacts, with clear contrast between the nonwoven fibers and the background. (General guidance would be choosing a voltage that is between 30 kv to 100 kv and with projection numbers above 1000). As an example, for the GE Pheonix vltomeix m CT scanner, the scanning parameters are: nanotube; voltage: 80 kV; current: 300 µA; tube mode: 3; timing: 1000 ms; averaging: 2; skip frames: 1; number of projections: 1500. The resulting data set is 2014×2014×2014 voxels with attenuation values represented as 16-bit integers. Each voxel has an edgewise dimension of 4 microns.

Figure 15:
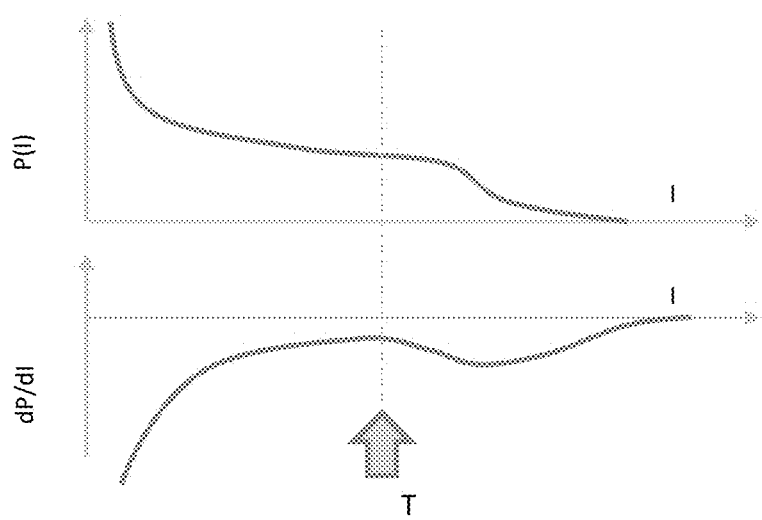
FIG. 15 illustrates one way of finding a suitable intensity threshold for discriminating fibers from air in 3D CT scan data, based on the first derivative of the intensity distribution.

The second stage of the test procedure is to preprocess the CT scan data, ready for the FSOI calculation. The fiber coordinates are calculated from micro-CT images through the following steps:

1. Re-orient micro-CT data to align MD and CD directions to be in x-y plane. In other words, align the x-y plane of the CT scan data with the x-y plane of the nonwoven web.
2. Across the entire 16-bit range of possible intensity values I, determine an intensity cutoff threshold, T, to extract the fiber coordinates. Any reasonable choice of threshold will work, as the subsequent steps are robust to slight overestimation or underestimation of the number of fiber voxels. In one preferred approach the cutoff is determined by finding the local minimum in the absolute derivative ldP/dIl of the intensity distribution function P(I). This works by finding the flattest point in the middle of the intensity distribution P(I), as illustrated in FIG. 15. Convert the voxel data to binary (1-bit) data using the determined threshold T. Any voxels having an intensity, I, above the threshold, T, are marked as being part of a fiber; any voxels having an intensity, I, below the threshold, T, are marked as empty.
3. Shrink the fiber thickness to one voxel by the method of morphological skeletonization. The skeleton is a medial axis representation of a shape in a 2-D image or 3-D space. The present method uses the following implementation of skeletonization: T.-C. Lee, R. L. Kashyap and C.-N. Chu, Building skeleton models via 3-D medial surface/axis thinning algorithms. *Computer Vision, Graphics, and Image Processing*, 56(6):462-478, 1994.
4. Delete isolated voxels, which are not part of a fiber. These are treated as noise.
5. In the 3D matrix data, the maximum distance between adjacent voxels will be $\sqrt{3}$ (voxel units). Therefore, voxel pairs with a distance of less than −3 between the voxels are considered as adjacent voxels in one fiber. Voxels determined to have 3 or more adjacent voxels are treated as artifacts from the skeletonization algorithm, and are removed.

The third stage of the procedure is to calculate the fiber orientation distribution from the fibers remaining in the preprocessed CT data. This is done in the following steps:

1. The connections of fiber coordinate voxels are determined by mutual distances, i.e. voxel pairs with a distance of less than −3 between the voxels are connected as adjacent voxels in a fiber.
2. Divide all fibers into segments of length 0.1 mm.
3. The segments are projected into the x-y plane and the x-y plane orientation of each segment-projection is calculated. Each segment is characterized by the vector (in the x-y plane) that joins the x-y-plane projections of the endpoints of that segment. This results in a set of vectors, one vector per segment. The vectors are defined such that they all lie in one half-plane (for example, so that all vectors have an orientation α, from 0° to +180°). This amounts to selecting the start and end of the vectors consistently—for example selecting the start of each vector as the endpoint that has the lower y-coordinate.

4. Divide the vectors into 18 bins of 100 each, based on their orientation angle α ($bin_1$: 0°≤α≤10°; $bin_2$: 10°≤α≤20°; bin3: 20°≤α≤30°; . . . ; bin18: 170°≤α≤180°). An orientation distribution is then calculated from the 18 bins, with one data point per bin. For each bin, the distribution value is calculated from the ratio of the number of vectors in the current bin to the total number of all vectors in all bins. The result is plotted as a normalized polar orientation histogram, with 18 bins. The value of each bin represents the proportion of fiber-segments falling into that bin.

5. Fit an ellipse to the histogram data plotted in polar coordinates, but the ellipse is defined in cartesian coordinates overlaid on the polar axes. The ellipse fitting method uses a parameter constraint conic fitting method as described in Fitzgibbon et al. (A. W. Fitzgibbon, M. Pilu and R. B. Fisher, "*Direct Least Squares Fitting of Ellipses*", Department of Artificial Intelligence, The University of Edinburgh, January 1996).

6. Calculate the FSOI as the ratio of the length of the minor axis of the ellipse to the length of the major axis of the ellipse.

Figure 9:
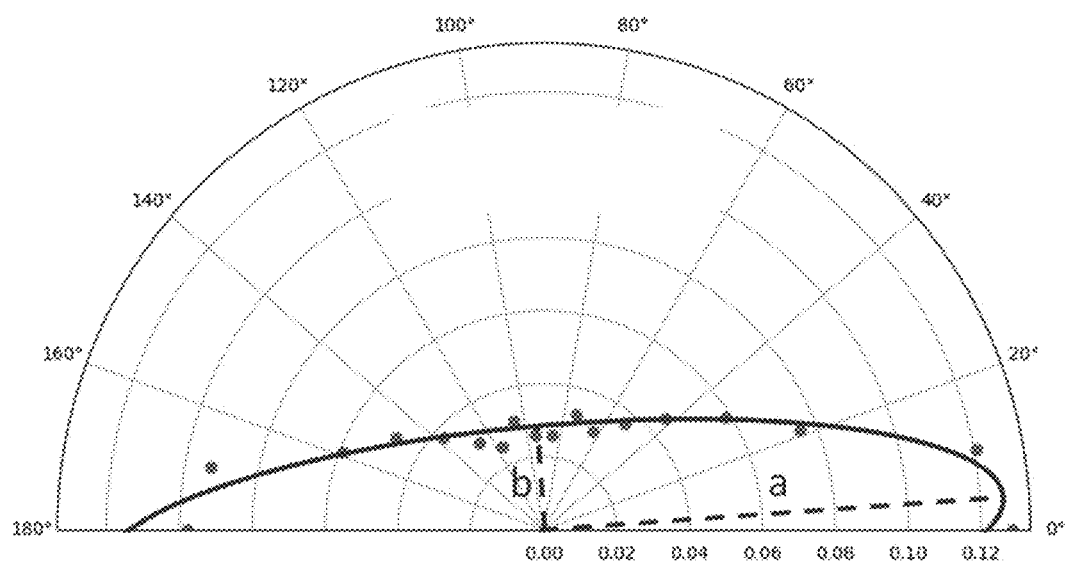
FIG. 9 is an exemplary distribution of fiber segments in a sample of apertured carded through air bonded nonwoven, according to an example.

An exemplary polar plot of the orientation distribution is shown in FIG. 9. The data points derived from the 18 bins are shown by dots and the resulting fitted ellipse curve is drawn on the diagram. The radial distance of each dot from the origin represents the value associated with that histogram bin—i.e. the proportion of fiber-segments that have the relevant orientation. As described in step 6 above, the FSOI is calculated by the ratio of b and a:b/a. This metric is rotationally invariant. Therefore, as can be seen in the plot of FIG. 9, the machine direction (MD) does not need to be aligned with the x-axis of the sample. The dominant orientation of the fiber segments will typically be in the machine direction, because of the way that the carded nonwoven is produced. Consequently, in practice, the major axis of the ellipse will generally align with the machine direction (MD).

Aperture Side Wall Height

Figure 10:
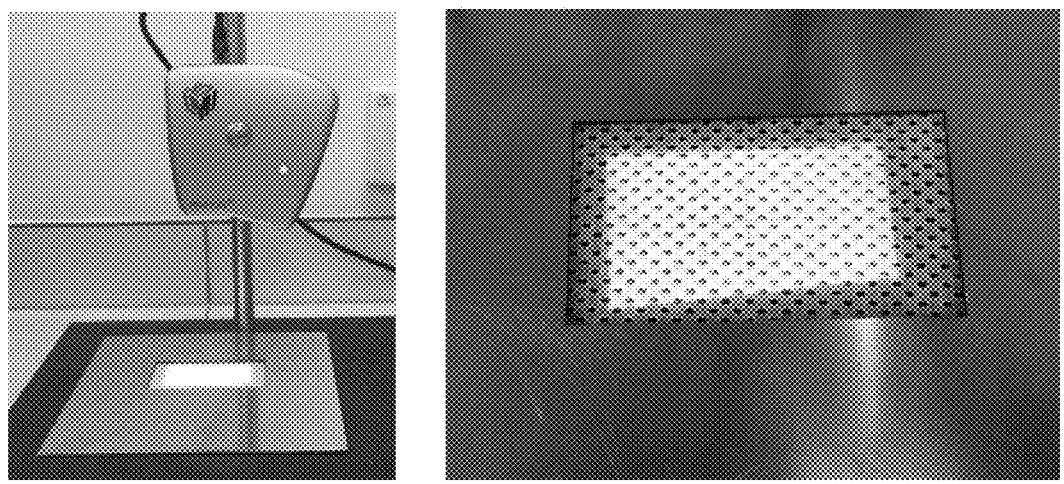
FIG. 10 shows an apparatus for measuring aperture side wall height.
Figure 11:
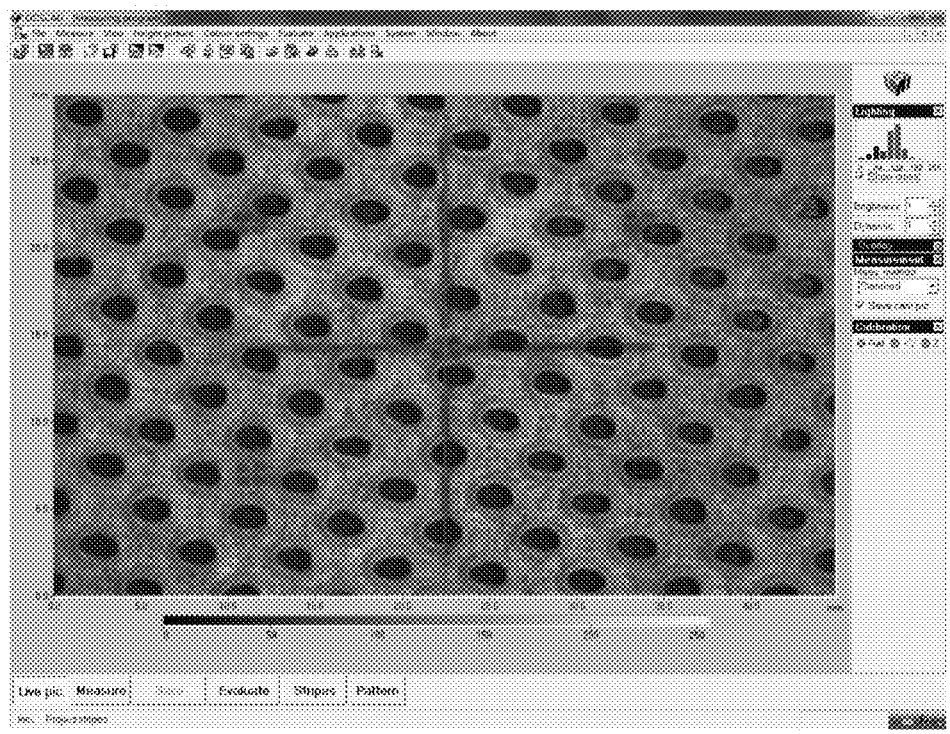
FIG. 11 is a screenshot from 3D image analysis software, for measuring aperture side wall height.
Figure 12:
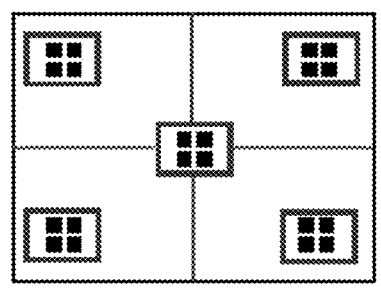
FIG. 12 illustrates a correct focusing condition when using the software of FIG. 11.
Figure 13:
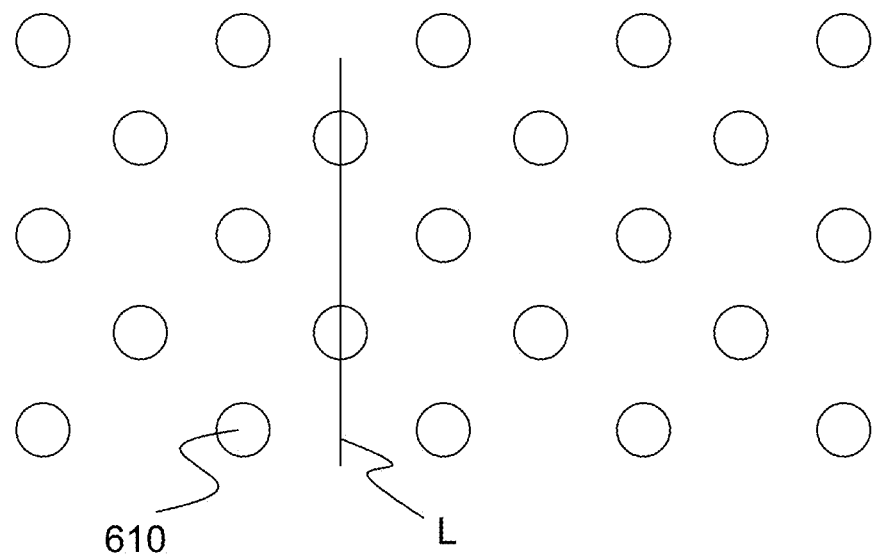
FIG. 13 schematically illustrates analysis of a nonwoven web using the software of FIG. 11.
Figure 14:
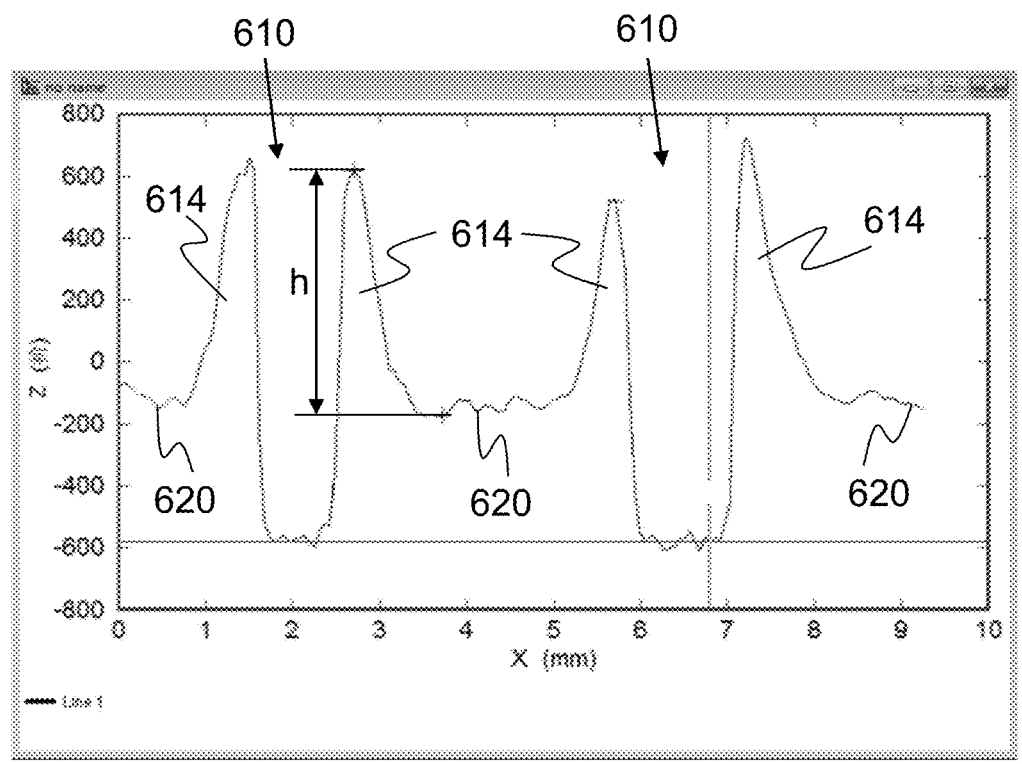
FIG. 14 shows a cross-section of a 3D scanned surface of the nonwoven web.

Apparatus: 3D scanner such as PRIMOS lite, 510045B-LED-W-PH, from LMI Technologies GmbH (Warthestrasse 32, 14513 Teltow/Berlin), or equivalent.
Software: ODSCAD 6.3 Rev. 7 2016/3/8, or equivalent.
Procedure:
1. Cut a piece of the nonwoven material with dimensions 10 cm×20 cm.
2. Keep the sample at a temperature/relative humidity of 23±2° C./50%±5% rH for 4 hours without tension or pressure.
3. Put the sample on the test platform of the 3D scanner, with the second surface (aperture-side wall side) facing upwards.
4. Gently apply a plate with a 5 cm×9 cm testing window on the sample, as shown in FIG. 10. (The testing window is a rectangular opening in the plate.)
5. Turn on the 3D scanner and open the ODSCAD software. Make sure calibration is validated.
6. Start measurement by clicking "Start measurement program" in the "Applications" menu in the software.
7. Turn on the projection light by clicking "Live picture", as shown in FIG. 11, and place the sample under the light projection field.
8. Adjust the brightness if the background is too dark. Select "Crosshair" under "Pattern" button and adjust the height of scanner to get the projected and the blended in crosshairs to coincide with one another, which should be the same as illustrated in FIG. 12, to focus the sample.
9. Capture the 3D profile by clicking "Measure", and save the 3D image to a computer file with "sample ID.omc" extension, by clicking "Save"
10. Open the saved image in "Open document" from the "Application" menu, and click the "Evaluation" button. Select to filter the image using the "polynomial filter material part". Apply the following settings: Rank n=6; Exclude material part valley %: 10; Exclude material part peak %: 20; Number of cycles: 1; Factor k: 1.00. Then, click the "Calculate" button.
11. Draw a line L across two apertures 610, as shown in FIG. 13, using the software drawing tools.
12. Click "Show sectional picture" in the "view" menu.
13. In the cross-sectional plot, measure the vertical (z-direction) distance between the aperture side wall and non-apertured area, which is recorded as the aperture side wall height, h. For each aperture, the height is measured on two opposing sides of the aperture (along the line L), corresponding to the two peaks in the cross-section. The z-direction distance is measured for each peak and for the lowest point of the non-apertured (land) area on the respective side of the aperture. This is illustrated in FIG. 14.
14. Repeat the measurement for 10 apertures (20 height-difference measurements)
15. Calculate the aperture side wall height as the mean of the 20 measurements.

Total Open Area Percentage

Apparatus: 3D scanner, such as PRIMOS lite, 510045B-LED-W-PH, from LMI Technologies GmbH (Warthestrasse 32, 14513 Teltow/Berlin), or equivalent.
Software: ODSCAD 6.3 Rev. 7 2016/3/8, or equivalent.
Procedure:
1. Cut a piece of the nonwoven material with dimensions 10 cm×20 cm.
2. Keep the sample at a temperature/relative humidity of 23±2° C./50%±5% rH for 4 hours without tension or pressure.
3. Put the sample on the test platform of the 3D scanner, with the first surface facing upwards (that is, with the aperture side walls facing downwards).
4. Gently apply a plate with a 5 cm×9 cm testing window on the sample, as shown in FIG. 10. (The testing window is a rectangular opening in the plate.)
5. Turn on the 3D scanner and open the ODSCAD software. Make sure calibration is validated.
6. Start measurement by clicking "Start measurement program" in the "Applications" menu in the software.
7. Turn on the projection light by clicking "Live picture", as shown in FIG. 11, and place the sample under the light projection field.
8. Adjust the brightness if the background is too dark. Select "Crosshair" under "Pattern" button and adjust the height of scanner to get the projected and the blended in crosshairs to coincide with one another, which should be the same as illustrated in FIG. 12, to focus the sample.

9. Capture the 3D profile by clicking "Measure", and save the 3D image to a computer file with "sample ID.omc" extension, by clicking "Save"
10. Open the saved image in "Open document" from the "Application" menu, and click the "Evaluation" button.
11. Click the "settings for void area ratio calculation" button in the "system" menu, and set the parameters as follows: unselect all under the "Pre-filtering" page; under the "cut heights" page, set "Void area cut count: 1", "Cut height 1 in mm: −0.1000". This defines the apertures, by cutting from the 3D profile any surface that lies more than 0.1 mm below the level of the first surface. In this way, the size of each aperture is implicitly defined by the size of the opening in the first surface. The reference level for the first surface (at which height=0) is defined as the mean height of the pixels in the 3D scan.
12. Select "calculate void area ratio" in the "Evaluation" menu. The total open area percentage will be returned.

The total open area percentage is the total area of the apertures divided by the total area of the sample. In this method, the total area of the apertures corresponds to the area below the cut height. The total area of the sample is 35 mm×20 mm. In other words, the software evaluates the proportion of open area in a rectangular sample of size 35 mm×20 mm.

Area Per Aperture

Apparatus: Microscope, mode VHX-S550E, from KEYENCE CORPORATION, 1-3-14, Higashinakajima, Higashiyodogawa-ku, Osaka, 533-8555, Japan.

Software: ImageJ 1.49v, Wayne Rasband, National Institutes of Health, USA

Procedure:

1. Cut a piece of the nonwoven material with dimensions 10 cm×20 cm.
2. Take a microscope photo (micrograph) of this nonwoven sample from its first surface (that is, with the aperture side walls facing away from the viewer), using 50× magnification. Make sure there is one entire aperture in the view.
3. Use the ImageJ software to open the microscope photo.
4. Draw a straight line, by using the ImageJ drawing tool, on the scale rule of the microscope photo, and then click "Set Scale" in the "Analyze" menu, and input the actual length and unit shown on the scale rule in the "known distance" and "Unit of length", respectively.
5. Then click "OK".
6. Use the "freehand" tool in the software drawing tools to mark one aperture in the microscope photo, ensuring that the area of the opening at the first surface is marked (this is the maximum area of the aperture, for a typical conical aperture).
7. Select "Area" in the "Set measurements" button under the "Analyze" Menu.
8. Then, click "Measure" under the "Analyze" Menu. The aperture area is shown.
9. Repeat the test for at least 5 different apertures and calculate the mean value.

Staple Fiber Length

Measurements are made according to the standard, ASTM D5103-07(2018)

Crimp Number

Measurements are made according to China National Standard Method, GBT 14338-2008.

Further Examples of the Invention

A. A nonwoven web suitable for use in a disposable absorbent article,
the nonwoven web having a first surface and a second surface opposing the first surface,
the nonwoven web including a plurality of apertures, each apertures being defined by an opening in the first surface and a side wall,
the nonwoven web comprising greater than 50% by weight of thermoplastic fibers,
wherein the side walls of the apertures have a mean height of less than about 460 µm, and
a Fiber Segment Orientation Index of the nonwoven web is less than about 0.46.

B. The nonwoven web of Paragraph A, wherein the nonwoven web has a tensile modulus in the machine direction, at 4% strain, of at least 30 N/cm, optionally at least 33 N/cm, optionally at least 35 N/cm, and optionally 35 N/cm.

C. The nonwoven web of Paragraph A or B, wherein the mean height of the side walls of the apertures is less than 440 µm, optionally less than 390 µm, optionally less than 360 µm.

D. The nonwoven web of any of Paragraphs A-C, wherein the Fiber Segment Orientation Index of the nonwoven web is less than 0.41, optionally less than 0.35.

E. The nonwoven web of any of Paragraphs A-D, wherein the Fiber Segment Orientation Index of the nonwoven web is at least 0.05, optionally at least 0.1, 0.15, or 0.2.

F. The nonwoven web of any of Paragraphs A-E, wherein the nonwoven web has a basis weight in the range 10 to 60 g/m$^2$, optionally 20 to 40 g/m$^2$, optionally 30 to 40 g/m$^2$, optionally 35 g/m$^2$.

G. The nonwoven web of any of Paragraphs A-F, wherein the thermoplastic fibers have a linear density in the range 0.6 to 6.6 dtex, optionally 1.3 to 4.5 dtex, optionally 2.2 to 4.5 dtex.

H. The nonwoven web of any of Paragraphs A-G, wherein the nonwoven web is a through air bonded nonwoven web.

I. The nonwoven web of any of Paragraphs A-H, wherein the apertures have a mean area per aperture in the range 0.2 to 4 mm$^2$, optionally 0.5 to 2.4 mm$^2$, optionally 0.5 to 1.0 mm$^2$.

J. The nonwoven web of any of Paragraphs A-I, wherein the nonwoven web has a total open area percentage in the range 5% to 25%, optionally 8% to 21%, optionally, 8% to 14%.

K. The nonwoven web of any of Paragraphs A-J, wherein the thermoplastic fibers are staple fibers, optionally crimped multicomponent staple fibers, optionally crimped bicomponent staple fibers.

L. A method of producing a nonwoven web with apertures, the nonwoven web having a first surface and a second surface and being suitable for use in a disposable absorbent article, the method comprising:
providing a precursor web, comprising greater than 50% by weight of the web of thermoplastic fibers;

providing a pair of rolls comprising a male roll and a female roll, the male and female rolls defining a nip between them, the female roll having an external surface comprising a plurality of recesses, the male roll having an external surface comprising a plurality of pins, wherein the pins are configured to mate with the recesses in the vicinity of the nip as the male roll and the female roll rotate;

feeding the precursor web to the pair of rolls at a feed rate;

using the nip between the pair of rolls, creating apertures in the precursor web to thereby produce the nonwoven web, each apertures being defined by an opening in the first surface and a side wall; and taking the nonwoven web off the pair of rolls at a take-off rate, wherein the feed rate is different from the take-off rate, and the take-off rate divided by the feed rate defines a drawing ratio of at least 1.06, and wherein the side walls of the apertures have a mean height of less than 460 µm.

M. The method of Paragraph L, wherein the drawing ratio is at least 1.06.

N. The method of Paragraph L or M, wherein the drawing ratio is at most 1.2, optionally at most 1.15.

O. The method of any one of Paragraphs L-N, wherein one or both of the pair of rolls are heated.

P. The method of any one of Paragraphs L-O, wherein the male roll is heated to a higher temperature than the female roll.

Q. The method of any one of Paragraphs L-P, further comprising cooling the apertured web after it is taken off the pair of rolls.

R. An absorbent article comprising: a topsheet; a backsheet; and an absorbent core between the topsheet and the backsheet, wherein at least one of the topsheet and the backsheet comprises a nonwoven web as defined in any one of Paragraphs A-K.

S. An absorbent article comprising: a topsheet; a backsheet; and an absorbent core between the topsheet and the backsheet, wherein at least one of the topsheet and the backsheet comprises a nonwoven web produced by a method as defined in any one of Paragraphs L-Q.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web suitable for use in a disposable absorbent article, the nonwoven web comprising a first surface and a second surface opposing the first surface, the nonwoven web including a plurality of apertures, each of the apertures being defined by an opening in the first surface and a side wall, and the nonwoven web comprising greater than 50% by weight of thermoplastic fibers, wherein the side walls of the apertures have a mean height of less than 460 µm, and wherein a Fiber Segment Orientation Index of the nonwoven web is less than 0.46.

2. The nonwoven web of claim 1, wherein the nonwoven web has a tensile modulus in the machine direction, at 4% strain, of at least 30 N/cm.

3. The nonwoven web of claim 1, wherein the mean height of the side walls of the apertures is less than 440 µm.

4. The nonwoven web of claim 1, wherein the Fiber Segment Orientation Index of the nonwoven web is less than 0.41.

5. The nonwoven web of claim 1, wherein the Fiber Segment Orientation Index of the nonwoven web is at least 0.05.

6. The nonwoven web of claim 1, wherein the nonwoven web has a basis weight in the range of about 10 g/m² to about 60 g/m².

7. The nonwoven web of claim 1, wherein the thermoplastic fibers have a linear density in the range of about 0.6 dtex to about 6.6 dtex.

8. The nonwoven web of claim 1, wherein the nonwoven web is a through air bonded nonwoven web.

9. The nonwoven web of claim 1, wherein the apertures have a mean area per aperture in the range of about 0.2 mm² to about 4 mm².

10. The nonwoven web of claim 1, wherein the nonwoven web has a total open area percentage in the range of about 5% to about 25%.

11. The nonwoven web of claim 1, wherein the thermoplastic fibers are staple fibers.

12. An absorbent article comprising: a topsheet; a backsheet; and an absorbent core positioned between the topsheet and the backsheet, wherein at least one of the topsheet and the backsheet comprises the nonwoven web of claim 1.

13. A nonwoven web suitable for use in a disposable absorbent article, the nonwoven web comprising a first surface and a second surface opposing the first surface, wherein the nonwoven web is a through air bonded nonwoven web, the nonwoven web including a plurality of apertures, each of the apertures being defined by an opening in the first surface and a side wall, and the nonwoven web comprising greater than 50% by weight of thermoplastic fibers, wherein the side walls of the apertures have a mean height of less than 460 µm, and wherein a Fiber Segment Orientation Index of the nonwoven web is less than 0.46.

* * * * *